United States Patent
Abdel-Magid et al.

(10) Patent No.: US 7,041,650 B2
(45) Date of Patent: May 9, 2006

(54) ANTICONVULSANT DERIVATIVE SALTS

(75) Inventors: Ahmed Abdel-Magid, Ambler, PA (US); Cynthia Maryanoff, Forest Grove, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/336,435

(22) Filed: Jan. 3, 2003

(65) Prior Publication Data

US 2003/0176362 A1 Sep. 18, 2003

Related U.S. Application Data

(63) Continuation-in-part of application No. 10/188,924, filed on Jul. 3, 2002.

(60) Provisional application No. 60/303,962, filed on Jul. 9, 2001.

(51) Int. Cl.
*A01N 43/04* (2006.01)
*A61K 31/70* (2006.01)
*C07H 1/00* (2006.01)

(52) U.S. Cl. .................. 514/23; 514/454; 514/455; 514/459; 514/463; 536/1.11; 536/18.7

(58) Field of Classification Search ................ 514/23, 514/439, 455, 419, 463; 536/1.11, 18.7
See application file for complete search history.

(56) References Cited

U.S. PATENT DOCUMENTS

| | | | |
|---|---|---|---|
| 4,513,006 A | | 4/1985 | Maryanoff et al. |
| 5,242,942 A | * | 9/1993 | Costanzo et al. ............ 514/439 |
| 5,384,327 A | | 1/1995 | Costanzo et al. |
| 5,498,629 A | * | 3/1996 | Costenzo et al. ............ 514/439 |
| 5,998,380 A | | 12/1999 | Ehrenberg et al. |
| 6,323,236 B1 | * | 11/2001 | McElroy ..................... 514/439 |
| 6,503,884 B1 | * | 1/2003 | Ehrenberg et al. ............ 514/23 |
| 6,559,293 B1 | * | 5/2003 | Almarsson et al. ......... 536/18.7 |

FOREIGN PATENT DOCUMENTS

| | | |
|---|---|---|
| WO | WO 00/07583 | 2/2000 |
| WO | WO 00/50020 | 8/2000 |
| WO | WO 03/006467 A | 1/2003 |
| WO | WO 03/070738 A | 8/2003 |

OTHER PUBLICATIONS

Faught, E., et al., Epilepsia, 36 (S4) 33, 1995.
Sachdeo, S.K. et al., Epilepsia, 36 (S4), 33, 1995.
International Search Report for Application No. PCT/US02/21016 dated Sep. 26, 2002.

* cited by examiner

*Primary Examiner*—James O. Wilson
*Assistant Examiner*—Traviss C. McIntosh, III
(74) *Attorney, Agent, or Firm*—Mary Appollina

(57) ABSTRACT

The invention relates to novel pharmaceutically acceptable salts of anticonvulsant derivatives, processes for preparation of and pharmaceutical compositions containing said salts, useful in the treatment of epilepsy.

9 Claims, No Drawings

ANTICONVULSANT DERIVATIVE SALTS

CROSS REFERENCE TO RELATED APPLICATION

This application is a continuation in part of U.S. non-provisional application Ser. No. 10/188,924 filed Jul. 03, 2002 which claims priority from U.S. provisional application Ser. No. 60/303,962 filed Jul. 09, 2001, the contents of which are hereby incorporated by reference.

FIELD OF THE INVENTION

The present invention relates to novel pharmaceutically acceptable salts of anticonvulsant derivatives, processes for preparation of and pharmaceutical compositions containing said salts.

BACKGROUND OF THE INVENTION

U.S. Pat. No. 4,513,006, which is hereby incorporated by reference, discloses a class of novel anti-epileptic compounds. One of these compounds, 2,3,4,5-bis-O-(1-methyl-ethylidene)-β-D-fructopyranose sulfamate, known as topiramate, has been demonstrated in clinical trials of human epilepsy to be effective as adjunctive therapy or as monotherapy in treating simple and complex partial seizure and secondarily generalized seizures (E. Faught, B. J. Wilder, R. E. Ramsey, R. A. Reife, L. D. Kramer, G. Pledger, R. M. Karim, et al., *Epilepsia*, 36 (S4) 33, (1995); S. K. Sachdeo, R. C. Sachdeo, R. A. Reife, P. Lim and G. Pledger, *Epilepsia*, 36 (S4) 33, (1995)). U.S. Pat. No. 4,513,006, No. 5,242,942, and No. 5,384,327, which are hereby incorporated by reference, disclose processes for the preparation of these novel anti-epileptic compounds.

Topiramate is currently marketed for the treatment of simple and complex partial seizure epilepsy with or without secondary generalized seizures in Great Britain, Finland, the United States and Sweden and applications for regulatory approval are presently pending in numerous countries throughout the world.

Ehrenberg et al in U.S. Pat. No. 5,998,380 disclose pharmaceutically acceptable derivatives of the following formula (A)

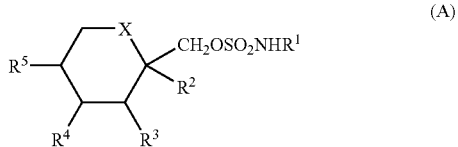

(A)

wherein the substituents are a described in U.S. Pat. No. 5,998,380. By pharmaceutically acceptable derivative is meant any pharmaceutically acceptable ester or salt of such ester of the compounds of the formula (A) or any other compounds which upon administration to the recipient is capable of providing (directly or indirectly) a compound of the formula (A) or an anti-migraine active metabolite or residue thereof.

Pharmaceutically acceptable salts of the compounds of the formula (A) include those derived from pharmaceutically acceptable, inorganic and organic acids and bases. Examples of suitable acids include hydrochloric, hydrobromic, sulfuric, nitric, perchloric, fumaric, maleic, phosphoric, glycollic, lactic, salicylic, succinic, toluene-p-sulphonic, tartaric, acetic, citric, formic, benzoic, malonic, naphthalene-2-sulphonic and benzenesulphonic acids. Other acids such as oxalic acid, while not in themselves pharmaceutically acceptable, may be useful in the preparation of salts useful as intermediates in obtaining compounds useful in the method of the patent and their pharmaceutically acceptable acid addition salts.

Salts derived from appropriate bases include alkali metal (e.g. sodium), alkaline earth metal (e.g. magnesium) ammonium and $NR_4$ (where R is $C_{1-4}$alkyl) salts.

McElroy, S. L. in PCT application WO 00/50020 disclose pharmaceutically acceptable salts of compounds of the following formula (B)

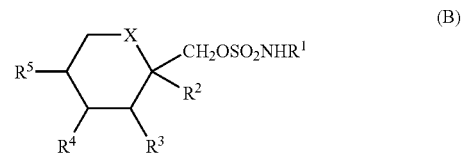

(B)

wherein the substituents are as described in PCT application WO 00/50020. Pharmaceutically acceptable salts of the compounds of the formula (B) include, for example, alkali metal salts, such as sodium and potassium; ammonium salts, monoalkylammonium salts; dialkylammonium salts; trialkylammonium salts; tetraalkylammonium salts; and tromethamine salts. Hydrates and other solvates of the compound of the formula (B) are also included within the scope of compounds.

Pharmaceutically acceptable salts of the compounds of formula (B) can be prepared by reacting the compound of the formula (B) with an appropriate base and recovering the salt.

Dewey et al, in PCT application WO 00/07583 disclose pharmaceutically acceptable salts of topiramate. As defined in the specification, pharmaceutically acceptable salts include those salt-forming acids and bases which do not substantially increase the toxicity of the compound. Some examples of suitable salts include salts of mineral acids such as hydrochloric, hydroiodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, eg. p-toluenesulfonic acids, and the like.

We now describe novel salt forms of anticonvulsant derivatives, including novel salt forms of topiramate, which forms are suitable for use in the preparation of pharmaceutical formulations.

SUMMARY OF THE INVENTION

The present invention relates to novel salt forms of a compound of formula (I)

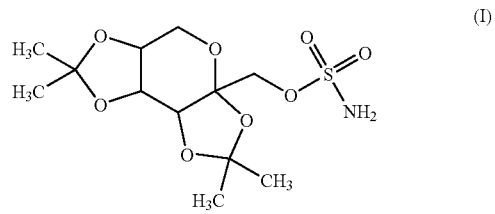

(I)

wherein the salts are formed at the sulfamate group of the compound of formula (I). Preferably the salts are formed by displacing at least one hydrogen on the sulfamate group of the compound of formula (I). More preferably, the salts are formed by displacing one hydrogen on the sulfamate group of the compound of formula (I)

In an embodiment, the present invention is directed to novel salt forms of topiramate, a compound of formula (Ia)

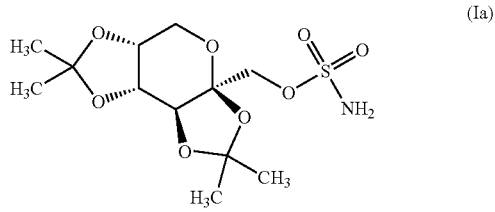

(Ia)

wherein the salts are formed at the sulfamate group of the compound of formula (Ia).

In an embodiment of the invention are alkali metal and magnesium salts of the compound of formula (I), formed at the sulfamate group of the compound of formula (I). Preferably, the compound of formula (I) is the compound of formula (Ia).

In an embodiment of the invention is a sodium salt of the compound of formula (I). In another embodiment of the invention is a potassium salt of the compound of formula (I). In still another embodiment of the invention is a lithium salt of the compound of formula (I). In still another embodiment of the invention is a magnesium salt of the compound of formula (I).

In an embodiment of the invention is a sodium salt of topiramate (the compound of formula (Ia)). In another embodiment of the invention is a potassium salt of topiramate (the compound of formula (Ia)). In still another embodiment of the invention is a lithium salt of topiramate (the compound of formula (Ia)). In still another embodiment of the invention is a magnesium salt of topiramate (the compound of formula (Ia)).

In an embodiment of the present invention is a choline salt of the compound of formula (I). In another embodiment of the present invention is a choline salt of topiramate (the compound of formula (Ia)).

In an aspect, the present invention relates to a process for preparing said salts of the compound of formula (I). In another aspect, the present invention relates to a process for preparing said salts of topiramate (the compound of formula (Ia)).

In a further aspect of the present invention are novel crystalline forms of the sodium, potassium and choline salts of topiramate, the compound of formula (Ia).

Illustrative of the invention is a pharmaceutical composition comprising any of the salts described above and a pharmaceutically acceptable carrier.

Exemplifying the invention is a pharmaceutical composition made by combining any of the salts described above and a pharmaceutically acceptable carrier.

An example of the invention is a process for making a pharmaceutical composition comprising combining any of the salts described above and a pharmaceutically acceptable carrier.

Another example of the invention is the use of any of the salts described herein in the preparation of a medicament for treating epilepsy, in a subject in need thereof.

DETAILED DESCRIPTION OF THE INVENTION

As used herein, unless otherwise noted, the term "anti-solvent" shall refer to a solvent which does not dissolve a specific substance and is added to a solution of said substance to cause precipitation of said substance.

As used herein, the term "alkyl" whether used alone or as part of a substituent group, includes straight and branched carbon chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1–4 carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, "lower" when used with alkoxy means an oxygen ether radical of a carbon chain composition of 1–4 carbon atoms.

The novel crystalline salts forms of the compound of formula (Ia) of the present invention were characterized by their respective X-ray powder diffraction (XRD) patterns utilizing a Phillips PW3710 based X-ray powder diffractometer, using a long fine-focus Cu $K_\alpha$ radiation source and the following system conditions:

a) CuKα radiation, 1.5406 Å, 40 KV, 30 mA
b) Optics: $1/12°$ divergence slit 0.2 mm receiving slit
c) Xenon gas-filled proportional detector
d) Scan 2 to 35°2θ at a scan speed of 0.0163°2θ/sec (step side 0.020 °2θ)
e) Conventional Philips sample holder The present invention is directed to novel salts of a compound of formula (I), preferably, novel salt forms of a compound of formula (Ia); novel crystalline forms of the sodium, potassium and choline salts of the compound of formula (Ia); and processes for the preparation of salts of a compound of formula (I). Particularly, the novel salts of a compound of formula (I) are alkali metals, magnesium or choline salts, wherein an alkali metal cation, a magnesium cation or a choline cation displaces at least one hydrogen atom, preferably one hydrogen atom, on the sulfamate portion of the compound of formula (I). More particularly, the salts are sodium, potassium, lithium, magnesium and choline salts of a compound of formula (I), wherein a sodium, potassium, lithium, magnesium or choline cation displaces at least one hydrogen atom, preferably one hydrogen atom, on the sulfamate portion of the compound of formula (I).

In a preferred embodiment of the present invention, the compound of formula (I) is the compound of formula (Ia).

In an embodiment of the present invention, is a process for preparing the alkali metal salts of a compound of formula (I), comprising a.) reacting the compound of formula (I) with an alkali metal hydride, an alkali metal hydroxide, an alkali metal lower alkoxide, an alkali metal amide, or if the alkali metal is lithium alternatively with an alkyl lithium; and b.) precipitating the product.

More particularly, the compound of formula (I) is reacted with an alkali metal hydride, under anhydrous conditions; or with an alkali metal hydroxide; or with an alkali metal lower alkoxide, preferably under anhydrous conditions; or with an alkali metal amide, under anhydrous conditions; in an organic solvent; or when the alkali metal is lithium alternatively with an alkyl lithium, under anhydrous conditions; and the product is precipitated to yield the corresponding alkali metal salt.

In an embodiment of the present invention, is a process for preparing the magnesium salts of a compound of formula (I), comprising a.) reacting the compound of formula (I) with a magnesium lower alkoxide; under anhydrous conditions; and b.) precipitating the product.

More particularly, the compound of formula (I) is reacted with a magnesium lower alkoxide, under anhydrous conditions; in an organic solvent; and the product is precipitated to yield the corresponding magnesium salt.

In one embodiment of the invention is a sodium salt of a compound of formula (I). Preferably, the sodium salt of the compound of formula (I) is a salt wherein a sodium cation displaces one of the hydrogen atoms of the sulfamate of the compound of formula (I).

Preferably, the sodium salt of the compound of formula (I) is a sodium salt of topiramate, the compound of formula (Ia).

Preferably, the sodium salt of topiramate is a compound of formula (II)

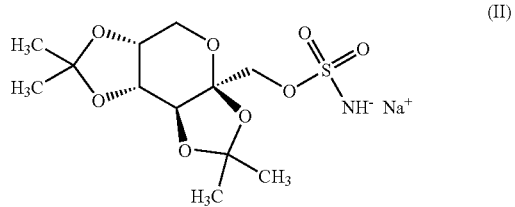

(II)

wherein a sodium cation displaces one of the hydrogen atoms of the sulfamate of the compound of formula (Ia).

In a further embodiment of the present invention is a process for preparing the sodium salt of a compound of formula (I), preferably topiramate, a compound of formula (Ia), comprising a.) reacting the compound of formula (I) with sodium hydride, sodium hydroxide, sodium lower alkoxide or sodium amide; in an organic solvent; or alternatively when the compound of formula (I) is reacted with sodium hydroxide or sodium lower alkoxide in an alcohol; and b.) precipitating the product.

More particularly, the compound of formula (I) is reacted with sodium hydride, under anhydrous conditions, in an inert organic solvent such as THF, Et$_2$O, toluene, t-butyl methyl ether (MTBE), and the like, preferably THF; and the product is precipitated.

Alternatively, the compound of formula (I) is reacted with sodium hydroxide, in an organic solvent such as THF, Et$_2$O, MTBE, ethyl acetate, isopropyl acetate, methanol, ethanol, and the like; or in a mixture of organic solvents such as methanol/ethyl acetate, methanol/isopropyl acetate, ethanol/ethyl acetate, ethanol/isopropyl acetate, and the like; and the product is precipitated.

Alternatively still, the compound of formula (I) is reacted with a sodium lower alkoxide such as sodium methoxide, sodium ethoxide, sodium propoxide, sodium t-butoxide, and the like; preferably sodium methoxide, preferably under anhydrous conditions, in an organic solvent such as THF, Et$_2$O, MTBE, ethyl acetate, isopropyl acetate, methanol, ethanol, and the like, or in a mixture organic solvents such as methanol/ethyl acetate, methanol/isopropyl acetate, ethanol/ethyl acetate, ethanol/isopropyl acetate, and the like, preferably in a mixture of methanol/isopropyl acetate; and the product is precipitated.

Alternatively still, the compound of formula (I) is reacted with sodium amide, under anhydrous conditions, in an organic solvent such as THF, Et$_2$O, and the like; and the product is precipitated.

The sodium salt product may be precipitated with an anti-solvent such as hexane, pentane, heptane, cyclohexane, and the like, preferably hexane, preferably at a reduced temperature in the range of about 25 to about −20° C. Alternatively, the sodium salt product may be precipitated by evaporation of the solvent.

The sodium salt product may be crystallized or recrystallized from an organic solvent such as ethyl acetate, methyl acetate, isopropyl acetate, and the like, or from a mixture of an alcohol and an organic solvent such as methanol/ethyl acetate, methanol/isopropyl actetate, ethanol/isopropyl acetate, ethanol/ethyl actetate, and the like, preferably from ethyl acetate or isopropyl acetate; optionally heating to fully dissolve the solid; adding water, preferably in an amount equal to or greater than about 2 equivalents, more preferably in an amount equal to about 3–5 equivalents, most preferably in an amount equal to about 3 equivalents; and cooling.

Alternatively, the sodium salt product may be crystallized or recrystallized from an organic solvent such as ethyl acetate, methyl acetate, isopropyl acetate, and the like, or from a mixture of an alcohol and an organic solvent such as methanol/ethyl acetate, methanol/isopropyl acetate, ethanol/isopropyl acetate, ethanol/ethyl acetate, and the like, preferably from ethyl acetate; by heating to fully dissolve the solid and then cooling.

In another embodiment of the invention is a potassium salt of a compound of formula (I). Preferably, the potassium salt of the compound of formula (I) is a salt wherein a potassium cation displaces one hydrogen atom of the sulfamate of the compound of formula (I)

Preferably, the potassium salt of the compound of formula (I) is a potassium salt of topiramate, the compound of formula (Ia).

Preferably, the potassium salt of topiramate, the compound of formula (Ia), is a compound of formula (III)

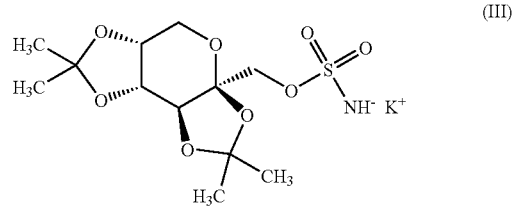

(III)

wherein a potassium cation displaces one hydrogen atom of the sulfamate of the compound of formula (Ia).

In a further embodiment of the present invention is a process for preparing the potassium salt of a compound of formula (I), preferably topiramate, a compound of formula (Ia), comprising a.) reacting the compound of formula (I) with potassium hydride, potassium hydroxide, potassium lower alkoxide or potassium amide, in an organic solvent or alternatively when the compound of formula (I) is reacted with potassium hydroxide or potassium lower alkoxide, in an alcohol; and b.) precipitating the product.

More particularly, the compound of formula (I) is reacted with potassium hydride, under anhydrous conditions, in an inert organic solvent such as THF, Et$_2$O, MTBE, toluene, and the like, preferably THF; and the product is precipitated.

Alternatively, the compound of formula (I) is reacted with potassium hydroxide, in an organic solvent such as THF, Et₂O, MTBE, ethyl acetate, isopropyl acetate, methanol, ethanol, and the like, or in a mixture of organic solvents such as methanol/ethyl acetate, methanol/isopropyl acetate, ethanol/ethyl acetate, ethanol/isopropyl acetate, and the like, preferably in an alcohol such as ethanol; and the product is precipitated.

Alternatively still, the compound of formula (I) is reacted with a potassium lower alkoxide such as potassium methoxide, potassium ethoxide, potassium propoxide, potassium t-butoxide, and the like, preferably potassium ethoxide; preferably under anhydrous conditions, in an organic solvent such as THF, Et₂O, MTBE, methanol, ethanol, and the like, or in a mixture of organic solvents such as methanol/ethyl acetate, methanol/isopropyl acetate, ethanol/ethyl acetate, ethanol/isopropyl acetate, and the like, preferably in ethanol; and the product is precipitated.

Alternatively still, the compound of formula (I) is reacted with potassium amide, under anhydrous conditions, in an inert organic solvent such as THF, Et₂O, and the like; and the product is precipitated.

The potassium salt product may be precipitated with an anti-solvent such as hexane, pentane, heptane, cyclohexane, and the like, preferably hexane, preferably at a reduced temperature in the range of about 25 to about −20° C. Alternatively, the potassium salt product may be precipitated by evaporation of the solvent.

The potassium salt product may be crystallized or recrystallized from an organic solvent such as ethyl acetate, methyl acetate, isopropyl acetate, methanol, ethanol, isopropyl alcohol, and the like, or from a mixture of organic solvents such as methanol/ethyl acetate, methanol/isopropyl actetate, ethanol/isopropyl acetate, ethanol/ethyl actetate, and the like, preferably from a mixture of ethyl acetate/methanol or ethanol, by heating to fully dissolve the solid, and cooling.

In another embodiment of the invention is a lithium salt of a compound of formula (I). Preferably, the lithium salt of the compound of formula (I) is a salt wherein a lithium cation displaces one hydrogen atom of the sulfamate of the compound of formula (I).

Preferably, the lithium salt of the compound of formula (I) is a lithium salt of topiramate, the compound of formula (Ia).

Preferably, the lithium salt of topiramate is a compound of formula (IV)

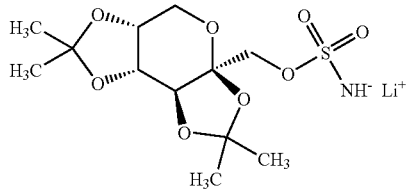

(IV)

wherein a lithium cation displaces one hydrogen atom of the sulfamate of the compound of formula (Ia).

In a further embodiment of the present invention is a process for preparing the lithium salt of a compound of formula (I), preferably topiramate, a compound of formula (Ia), comprising a.) reacting the compound of formula (I) with lithium hydride, lithium hydroxide, lithium lower alkoxide, alkyl lithium or lithium amide, in an organic solvent or alternatively when the compound of formula (I) is reacted with lithium hydroxide or lithium lower alkoxide, in an alcohol; and b.) precipitating the product.

More particularly, the compound of formula (I) is reacted with lithium hydride, under anhydrous conditions, in an inert organic solvent such as THF, Et₂O, MTBE, and the like, preferably THF; and the product is precipitated.

Alternatively, the compound of formula (I) is reacted with lithium hydroxide, in an organic solvent such as THF, Et₂O, MTBE, ethyl acetate, isopropyl acetate, methanol, ethanol, and the like, or in a mixture of organic solvents such as methanol/ethyl acetate, methanol/isopropyl acetate, ethanol/ethyl acetate, ethanol/isopropyl acetate, and the like; preferably under anhydrous conditions, and the product is precipitated.

Alternatively still, the compound of formula (I) is reacted with a lithium lower alkoxide such as lithium methoxide, lithium ethoxide, lithium propoxide, lithium t-butoxide, and the like; preferably under anhydrous conditions, in an organic solvent such as THF, Et₂O, MTBE, methanol, ethanol, and the like, or in a mixture of organic solvents such as methanol/ethyl acetate, methanol/isopropyl acetate, ethanol/ethyl acetate, ethanol/isopropyl acetate, and the like; and the product is precipitated.

Alternatively still, the compound of formula (I) is reacted with an alkyl lithium such as methyl lithium, ethyl lithium, n-butyl lithium, and the like, preferably n-butyl lithium; under anhydrous conditions, in an inert organic solvent such as THF, Et₂O, MTBE, and the like; and the product is precipitated.

Alternatively still, the compound of formula (I) is reacted with lithium amide, under anhydrous conditions, in an inert organic solvent such as THF, Et₂O, and the like; and the product is precipitated.

The lithium salt product may be precipitated by evaporation of the solvent.

In another embodiment of the invention is a magnesium salt of a compound of formula (I). Preferably, the magnesium salt of the compound of formula (I) is a salt wherein a magnesium cation displaces one hydrogen atom of the sulfamate of the compound of formula (I).

Preferably, the magnesium salt of the compound of formula (I) is a magnesium salt of topiramate, the compound of formula (Ia).

Preferably, the magnesium, salt of topiramate is a compound of formula (V):

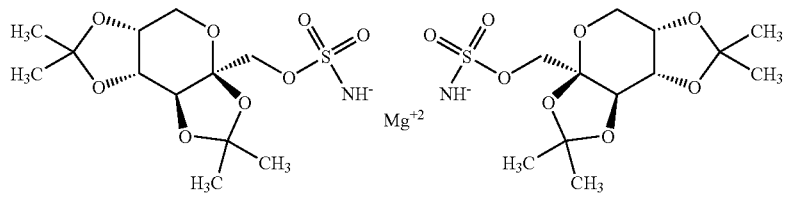

(V)

wherein a magnesium cation displaces one hydrogen atom of the sulfamate of two molecules of the compound of formula (Ia).

In a further embodiment of the present invention is a process for preparing a magnesium salt of a compound of formula (I), preferably topiramate, a compound of formula (Ia), comprising a.) reacting the compound of formula (I) with magnesium lower alkoxide; under anhydrous conditions; in an organic solvent; and b.) precipitating the product.

More particularly, the compound of formula (I) is reacted with a magnesium lower alkoxide, such as magnesium methoxide, magnesium ethoxide, magnesium-t-butoxide, and the like, preferably magnesium methoxide, under anhydrous conditions, in an organic solvent such as ethyl acetate, isopropyl acetate, THF, $Et_2O$, MTBE, methanol, ethanol, and the like, or in a mixture of organic solvents such as methanol/ethyl acetate, methanol/isopropyl acetate, ethanol/ethyl acetate, ethanol/isopropyl acetate, and the like, preferably in methanol; and precipitating the product.

The magnesium salt product may be precipitated with an anti-solvent such as hexane, pentane, heptane, cyclohexane, and the like, preferably hexane, preferably at a reduced temperature in the range of about 25 to about −20° C. Alternatively, the magnesium salt product may be precipitated by cooling the solution to a temperature in the range of about 0 to about −20° C. Alternatively still, the magnesium salt product may be precipitated by evaporation of the solvent.

As used herein the term "choline" shall mean the choline cation, more particularly (2-hyroxyethyl)trimethylammonium ($C_5H_{14}NO$). The term "choline hydroxide" shall mean (2-hyrdoxyethyl)trimethylammonium hydroxide ($C_5H_{15}NO_2$).

In another embodiment of the invention is a choline salt of a compound of formula (I). Preferably, the choline salt of the compound of formula (I) is a salt wherein a choline cation displaces one hydrogen atom of the sulfamate of the compound of formula (I).

Preferably, the choline salt of the compound of formula (I) is a choline salt of topiramate, the compound of formula (Ia).

Preferably, the choline salt of topiramate is a compound of formula (VI):

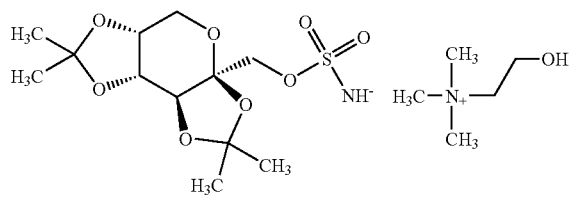

(VI)

wherein a choline cation displaces one hydrogen atom of the sulfamate of the compound of formula (Ia).

In a further embodiment of the present invention is a process for preparing a choline salt of a compound of formula (I), preferably topiramate, a compound of formula (Ia), comprising c.) reacting the compound of formula (I) with choline hydroxide; in an organic solvent; and d.) precipitating the product.

More particularly, the compound of formula (I) is reacted with choline hydroxide, in an organic solvent such as ethyl acetate, isopropyl acetate, THF, $Et_2O$, MTBE, methanol, ethanol, and the like, or in a mixture of organic solvents such as methanol/ethyl acetate, methanol/isopropyl acetate, ethanol/ethyl acetate, ethanol/isopropyl acetate, and the like, preferably in a mixture of ethyl acetate/methanol; and precipitating the product.

The choline salt product may be precipitated by evaporation of the solvent.

The choline salt product may be crystallized or recrystallized from an organic solvent such as ethyl acetate, methyl acetate, isopropyl acetate, methanol, ethanol, isopropyl alcohol, and the like, or from a mixture of organic solvents such as methanol/ethyl acetate, methanol/isopropyl actetate, ethanol/isopropyl acetate, ethanol/ethyl actetate, and the like, preferably from a mixture of ethyl acetate/methanol, by heating to fully dissolve the solid, and cooling.

The present invention further relates to novel crystalline forms of the compound of formula (II), the compound of formula (III) and the compound of formula (VI); and amorphous forms of the compound of formula (II), the compound of formula (III), the compound of formula (IV), the compound of formula (V) and the compound of formula (VI).

In an embodiment of the present invention are novel crystalline forms of the compound of formula (II), more particularly Form Na1 and Form Na2; and amorphous Form Na4.

Amorphous Form Na4 of the compound of formula (II) may be characterized by its physical appearance (foamy solid) and the absence of narrow peaks in the XRD (no XRD pattern).

Amorphous Form Na4 may be prepared by reacting the compound of formula (II) with sodium hydroxide, in an organic solvent, and precipitating the product by treating the solution with an anti-solvent or by evaporating the solvent under reduced pressure.

Crystalline Form Na1 of the compound of formula (II) may be characterized by its X-ray diffraction pattern, comprising the peaks:

TABLE 1

X-Ray Diffraction Peaks, Na Salt, Form Na1

| Angle (°2θ) | d-spacing (Ångstrom) | Relative Intensity (%) |
|---|---|---|
| 4.500 | 19.6206 | 100.0 |
| 9.020 | 9.7961 | 7.2 |
| 11.390 | 7.7625 | 1.2 |
| 12.065 | 7.3297 | 22.4 |
| 12.690 | 6.9701 | 8.5 |
| 13.530 | 6.5392 | 42.3 |
| 13.655 | 6.4796 | 42.3 |
| 14.975 | 5.9113 | 12.6 |
| 16.120 | 5.4939 | 4.8 |
| 16.900 | 5.2421 | 0.9 |
| 17.510 | 5.0608 | 10.9 |
| 18.040 | 4.9133 | 56.3 |
| 18.420 | 4.8128 | 2.9 |
| 19.065 | 4.6514 | 32.4 |
| 20.050 | 4.4250 | 8.7 |
| 20.745 | 4.2783 | 13.2 |
| 21.160 | 4.1953 | 2.7 |
| 21.710 | 4.0903 | 16.0 |
| 22.515 | 3.9458 | 17.0 |
| 23.600 | 3.7668 | 3.7 |
| 23.925 | 3.7164 | 11.3 |
| 24.445 | 3.6385 | 32.1 |
| 24.985 | 3.5611 | 1.7 |
| 25.665 | 3.4682 | 5.0 |
| 26.420 | 3.3708 | 7.8 |
| 27.315 | 3.2624 | 36.8 |
| 27.765 | 3.2105 | 18.0 |
| 28.260 | 3.1554 | 11.3 |
| 29.735 | 3.0021 | 12.9 |
| 30.065 | 2.9699 | 3.7 |
| 30.870 | 2.8943 | 12.2 |

TABLE 1-continued

X-Ray Diffraction Peaks, Na Salt, Form Na1

| Angle (°2θ) | d-spacing (Ångstrom) | Relative Intensity (%) |
|---|---|---|
| 31.355 | 2.8506 | 2.4 |
| 31.800 | 2.8117 | 7.3 |
| 32.805 | 2.7279 | 8.9 |
| 33.035 | 2.7094 | 7.0 |
| 33.640 | 2.6620 | 4.8 |
| 34.805 | 2.5755 | 18.2 |

Crystalline Form Na1 of the compound of formula (II) may be further characterized by its X-ray diffraction pattern, comprising the major peaks:

TABLE 2

X-Ray Diffraction Peaks, Na Salt, Form Na1

| Angle (°2θ) | d-spacing (Ångstrom) | Relative Intensity (%) |
|---|---|---|
| 4.500 | 19.6206 | 100.0 |
| 12.065 | 7.3297 | 22.4 |
| 13.530 | 6.5392 | 42.3 |
| 13.655 | 6.4796 | 42.3 |
| 14.975 | 5.9113 | 12.6 |
| 17.510 | 5.0608 | 10.9 |
| 18.040 | 4.9133 | 56.3 |
| 19.065 | 4.6514 | 32.4 |
| 20.745 | 4.2783 | 13.2 |
| 21.710 | 4.0903 | 16.0 |
| 22.515 | 3.9458 | 17.0 |
| 23.925 | 3.7164 | 11.3 |
| 24.445 | 3.6385 | 32.1 |
| 27.315 | 3.2624 | 36.8 |
| 27.765 | 3.2105 | 18.0 |
| 28.260 | 3.1554 | 11.3 |
| 29.735 | 3.0021 | 12.9 |
| 30.870 | 2.8943 | 12.2 |
| 34.805 | 2.5755 | 18.2 |

Crystalline Form Na1 may be prepared according to the process outlined above, reacting the compound of formula (Ia) with sodium hydride, sodium hydroxide or sodium lower alkoxide, in an organic solvent or mixture thereof; optionally evaporating the solvent to precipitate the product; and crystallizing or recrystallizing in an organic solvent such as ethyl acetate, isopropyl acetate, and the like or a mixture of organic solvents such as methanol/ethyl acetate, ethanol/ethyl acetate, methanol/isopropyl acetate, ethanol/isopropyl acetate, preferably methanol/isopropyl acetate, optionally heating to fully dissolve the solid, and then adding water, preferably in the amount equal to or greater than about 2 equivalents, more preferably in an amount equal to about 3–5 equivalents, most preferably in an amount equal to about 3 equivalents, and cooling.

Alternatively, crystalline Form Na1 may be prepared by subjecting amorphous form Na4 to elevated humidity conditions.

Crystalline Form Na2 of the compound of formula (II) may be characterized by its X-ray diffraction pattern, comprising the peaks:

TABLE 3

X-Ray Diffraction Peaks, Na Salt, Form Na2

| Angle (°2θ) | d-spacing (Ångstrom) | Relative Intensity (%) |
|---|---|---|
| 4.450 | 19.8409 | 7.6 |
| 5.080 | 17.3817 | 89.5 |
| 8.025 | 11.0084 | 3.7 |
| 8.805 | 10.0348 | 4.1 |
| 9.980 | 8.8559 | 2.5 |
| 11.545 | 7.6587 | 42.6 |
| 11.980 | 7.3815 | 7.4 |
| 12.375 | 7.1468 | 11.1 |
| 13.625 | 6.4938 | 71.9 |
| 15.255 | 5.8034 | 53.3 |
| 17.605 | 5.0337 | 13.3 |
| 17.990 | 4.9268 | 15.6 |
| 18.460 | 4.8024 | 14.3 |
| 19.040 | 4.6574 | 100.0 |
| 19.840 | 4.4714 | 11.4 |
| 21.115 | 4.2042 | 29.5 |
| 21.240 | 4.1797 | 19.2 |
| 22.325 | 3.9790 | 12.2 |
| 22.835 | 3.8913 | 15.8 |
| 23.890 | 3.7217 | 9.8 |
| 25.040 | 3.5534 | 17.4 |
| 25.665 | 3.4682 | 35.7 |
| 27.305 | 3.2635 | 11.4 |
| 28.060 | 3.1774 | 7.4 |
| 28.860 | 3.0911 | 8.6 |
| 29.555 | 3.0200 | 7.3 |
| 30.495 | 2.9290 | 12.2 |
| 31.740 | 2.8169 | 15.0 |
| 32.450 | 2.7569 | 7.4 |
| 32.980 | 2.7138 | 10.1 |
| 33.980 | 2.6362 | 8.8 |

Crystalline Form Na2 of the compound of formula (II) may be further characterized by its X-ray diffraction pattern, comprising the major peaks:

TABLE 4

X-Ray Diffraction Peaks, Na Salt, Form Na2

| Angle (°2θ) | d-spacing (Ångstrom) | Relative Intensity (%) |
|---|---|---|
| 5.080 | 17.3817 | 89.5 |
| 11.545 | 7.6587 | 42.6 |
| 12.375 | 7.1468 | 11.1 |
| 13.625 | 6.4938 | 71.9 |
| 15.255 | 5.8034 | 53.3 |
| 17.605 | 5.0337 | 13.3 |
| 17.990 | 4.9268 | 15.6 |
| 18.460 | 4.8024 | 14.3 |
| 19.040 | 4.6574 | 100.0 |
| 19.840 | 4.4714 | 11.4 |
| 21.115 | 4.2042 | 29.5 |
| 21.240 | 4.1797 | 19.2 |
| 22.325 | 3.9790 | 12.2 |
| 22.835 | 3.8913 | 15.8 |
| 25.040 | 3.5534 | 17.4 |
| 25.665 | 3.4682 | 35.7 |
| 27.305 | 3.2635 | 11.4 |
| 30.495 | 2.9290 | 12.2 |
| 31.740 | 2.8169 | 15.0 |
| 32.980 | 2.7138 | 10.1 |

Crystalline Form Na2 may be prepared by recrystallizing the crystalline Form Na1 from an anhydrous organic solvent, such as ethyl acetate, methyl acetate, isopropyl acetate, and the like, preferably ethyl acetate, without addition of water, by heating and cooling.

The crystalline form of the compound of formula (II), specifically Form Na1 is a tri-hydrate, whereas the crystalline form of the compound of formula (II), specifically Form Na2 is a non-hydrate, as determined by Karl-Fischer measurements of weight % water, as listed in Table 5.

TABLE 5

KARL-FISCHER VALUES, Na Salts

| Form | % Water Meas. | % Water Theor. | Hydrate Form |
|---|---|---|---|
| Na1 | 13.0–14.2% | 13% | tri-hydrate |
| Na2 | 1.64% | 0% | non-hydrate |

In another embodiment of the present invention are novel crystalline forms of the compound of formula (III), more particularly Form K1 and Form K2; and amorphous Form K3.

Amorphous Form K3 of the compound of formula (III) may be characterized by its physical appearance (foamy solid) and the absence of narrow peaks in the XRD (no XRD pattern).

Amorphous Form K3 may be prepared by reacting the compound of formula (Ia) with potassium hydroxide, in an organic solvent, and precipitating the product by evaporating the solvent.

Crystalline Form K1 of the compound of formula (III) may be characterized by its X-ray diffraction pattern, comprising the peaks:

TABLE 6

X-Ray Diffraction Peaks, K Salt, Form K1

| Angle (°2θ) | d-spacing (Ångstrom) | Relative Intensity (%) |
|---|---|---|
| 4.975 | 17.7483 | 100.0 |
| 5.830 | 15.1472 | 43.3 |
| 7.895 | 11.1893 | 6.5 |
| 9.940 | 8.8914 | 17.6 |
| 10.460 | 8.4505 | 3.1 |
| 11.695 | 7.5608 | 4.1 |
| 12.270 | 7.2077 | 4.6 |
| 12.730 | 6.9483 | 2.2 |
| 13.115 | 6.7452 | 2.7 |
| 13.560 | 6.5248 | 12.4 |
| 14.120 | 6.2673 | 1.1 |
| 14.930 | 5.9290 | 31.2 |
| 15.245 | 5.8072 | 27.2 |
| 15.835 | 5.5921 | 2.2 |
| 16.135 | 5.4888 | 1.5 |
| 17.225 | 5.1439 | 3.9 |
| 17.645 | 5.0224 | 7.2 |
| 17.915 | 4.9473 | 17.3 |
| 18.420 | 4.8128 | 2.8 |
| 18.660 | 4.7514 | 3.9 |
| 19.060 | 4.6526 | 2.0 |
| 19.355 | 4.5823 | 4.5 |
| 19.960 | 4.4448 | 9.5 |
| 20.890 | 4.2490 | 50.6 |
| 21.510 | 4.1279 | 3.0 |
| 21.995 | 4.0379 | 4.0 |
| 23.475 | 3.7866 | 15.0 |
| 25.210 | 3.5298 | 35.6 |
| 25.755 | 3.4563 | 5.0 |
| 26.525 | 3.3577 | 6.5 |
| 27.265 | 3.2682 | 2.3 |
| 27.975 | 3.1869 | 5.2 |
| 28.605 | 3.1181 | 4.2 |
| 29.535 | 3.0220 | 3.9 |
| 30.105 | 2.9661 | 18.4 |
| 30.290 | 2.9484 | 14.4 |
| 30.760 | 2.9044 | 4.7 |
| 31.265 | 2.8586 | 3.4 |
| 31.710 | 2.8195 | 4.4 |
| 32.630 | 2.7421 | 2.0 |
| 32.895 | 2.7206 | 2.9 |
| 33.810 | 2.6490 | 4.3 |
| 34.165 | 2.6223 | 7.2 |

Crystalline Form K1 of the compound of formula (III) may be further characterized by its X-ray diffraction pattern, comprising the major peaks:

TABLE 7

X-Ray Diffraction Peaks, K Salt, Form K1

| Angle (°2θ) | d-spacing (Ångstrom) | Relative Intensity (%) |
|---|---|---|
| 4.975 | 17.7483 | 100.0 |
| 5.830 | 15.1472 | 43.3 |
| 9.940 | 8.8914 | 17.6 |
| 13.560 | 6.5248 | 12.4 |
| 14.930 | 5.9290 | 31.2 |
| 15.245 | 5.8072 | 27.2 |
| 17.915 | 4.9473 | 17.3 |
| 20.890 | 4.2490 | 50.6 |
| 23.475 | 3.7866 | 15.0 |
| 25.210 | 3.5298 | 35.6 |
| 30.105 | 2.9661 | 18.4 |
| 30.290 | 2.9484 | 14.4 |

Crystalline Form K2 of the compound of formula (III) may be characterized by its X-ray diffraction pattern, comprising the peaks:

TABLE 8

X-Ray Diffraction Peaks, K Salt, Form K2

| Angle (°2θ) | d-spacing (Ångstrom) | Relative Intensity (%) |
|---|---|---|
| 4.430 | 19.9304 | 100.0 |
| 4.940 | 17.8739 | 8.1 |
| 5.785 | 15.2649 | 10.2 |
| 6.275 | 14.0739 | 11.9 |
| 7.020 | 12.5819 | 18.9 |
| 7.835 | 11.2749 | 4.4 |
| 9.430 | 9.3711 | 16.4 |
| 9.915 | 8.9138 | 5.1 |
| 11.345 | 7.7932 | 23.5 |
| 12.205 | 7.2460 | 6.7 |
| 12.715 | 6.9565 | 18.1 |
| 13.475 | 6.5658 | 24.4 |
| 13.805 | 6.4095 | 21.8 |
| 14.090 | 6.2805 | 15.5 |
| 14.875 | 5.9508 | 17.9 |
| 15.220 | 5.8167 | 12.4 |
| 15.505 | 5.7104 | 18.5 |
| 15.770 | 5.6150 | 23.8 |
| 16.495 | 5.3698 | 22.2 |
| 16.920 | 5.2359 | 15.6 |
| 17.355 | 5.1056 | 29.9 |
| 17.920 | 4.9459 | 22.9 |
| 18.495 | 4.7934 | 19.3 |
| 19.150 | 4.6309 | 18.7 |
| 19.795 | 4.4815 | 34.9 |
| 20.200 | 4.3925 | 50.1 |
| 20.780 | 4.2712 | 19.3 |
| 21.485 | 4.1326 | 13.2 |

TABLE 8-continued

X-Ray Diffraction Peaks, K Salt, Form K2

| Angle (°2θ) | d-spacing (Ångstrom) | Relative Intensity (%) |
|---|---|---|
| 21.975 | 4.0416 | 9.9 |
| 22.320 | 3.9799 | 19.1 |
| 22.705 | 3.9132 | 18.7 |
| 23.455 | 3.7898 | 11.1 |
| 24.040 | 3.6989 | 22.0 |
| 24.720 | 3.5986 | 12.5 |
| 25.070 | 3.5492 | 13.7 |
| 25.555 | 3.4829 | 16.2 |
| 25.995 | 3.4249 | 18.9 |
| 26.570 | 3.3521 | 10.8 |
| 27.240 | 3.2712 | 21.1 |
| 27.865 | 3.1992 | 19.1 |
| 28.330 | 3.1477 | 14.7 |
| 28.860 | 3.0911 | 12.0 |
| 29.285 | 3.0472 | 14.7 |
| 30.880 | 2.8934 | 15.1 |
| 31.965 | 2.7976 | 14.4 |
| 32.955 | 2.7158 | 9.6 |
| 34.235 | 2.6171 | 9.6 |

Crystalline Form K2 of the compound of formula (III) may be further characterized by its X-ray diffraction pattern, comprising the major peaks:

TABLE 9

X-Ray Diffraction Peaks, K Salt, Form K2

| Angle (°2θ) | d-spacing (Ångstrom) | Relative Intensity (%) |
|---|---|---|
| 4.430 | 19.9304 | 100.0 |
| 5.785 | 15.2649 | 10.2 |
| 6.275 | 14.0739 | 11.9 |
| 7.020 | 12.5819 | 18.9 |
| 9.430 | 9.3711 | 16.4 |
| 11.345 | 7.7932 | 23.5 |
| 12.715 | 6.9565 | 18.1 |
| 13.475 | 6.5658 | 24.4 |
| 13.805 | 6.4095 | 21.8 |
| 14.090 | 6.2805 | 15.5 |
| 14.875 | 5.9508 | 17.9 |
| 15.220 | 5.8167 | 12.4 |
| 15.505 | 5.7104 | 18.5 |
| 15.770 | 5.6150 | 23.8 |
| 16.495 | 5.3698 | 22.2 |
| 16.920 | 5.2359 | 15.6 |
| 17.355 | 5.1056 | 29.9 |
| 17.920 | 4.9459 | 22.9 |
| 18.495 | 4.7934 | 19.3 |
| 19.150 | 4.6309 | 18.7 |
| 19.795 | 4.4815 | 34.9 |
| 20.200 | 4.3925 | 50.1 |
| 20.780 | 4.2712 | 19.3 |
| 21.485 | 4.1326 | 13.2 |
| 21.975 | 4.0416 | 9.9 |
| 22.320 | 3.9799 | 19.1 |
| 22.705 | 3.9132 | 18.7 |
| 23.455 | 3.7898 | 11.1 |
| 24.040 | 3.6989 | 22.0 |
| 24.720 | 3.5986 | 12.5 |
| 25.070 | 3.5492 | 13.7 |
| 25.555 | 3.4829 | 16.2 |
| 25.995 | 3.4249 | 18.9 |
| 26.570 | 3.3521 | 10.8 |
| 27.240 | 3.2712 | 21.1 |
| 27.865 | 3.1992 | 19.1 |
| 28.330 | 3.1477 | 14.7 |
| 28.860 | 3.0911 | 12.0 |
| 29.285 | 3.0472 | 14.7 |
| 30.880 | 2.8934 | 15.1 |
| 31.965 | 2.7976 | 14.4 |

TABLE 9-continued

X-Ray Diffraction Peaks, K Salt, Form K2

| Angle (°2θ) | d-spacing (Ångstrom) | Relative Intensity (%) |
|---|---|---|
| 32.955 | 2.7158 | 9.6 |
| 34.235 | 2.6171 | 9.6 |

Crystalline Form K1 and Form K2 may be prepared by recrystallizing the amorphous Form K3. More particularly, crystalline Form K1 may be prepared by recrystallizing amorphous Form K3 from an organic solvent or mixture thereof, preferably an ethyl acetate/methanol mixture wherein the percent methanol is greater than or equal to about 5%, by heating and cooling.

Alternatively, crystalline Form K1 may be prepared by recrystallizing amorphous Form K3, crystalline Form K2 or a mixture thereof, from an organic solvent such as ethyl acetate, isopropyl acetate, ethanol, methanol, and the like, or from a mixture thereof, such as ethanol/isopropyl acetate, ethanol/ethyl acetate, and the like, preferably from ethanol, by heating and cooling.

Crystalline Form K2 may be prepared by recrystallizing amorphous Form K3 from an organic solvent or mixture thereof, preferably an ethyl acetate/methanol mixture wherein the percent methanol is less than about 5%, by heating and cooling.

Alternatively, crystalline Form K2 may be prepared by recrystallizing amorphous Form K3 from an organic solvent or mixture thereof, preferably an ethyl acetate/methanol mixture wherein the percent methanol is greater than about 5%, by heating the mixture to evaporate excess methanol, as measured by an increase in boiling temperature to greater than about 70° C. and cooling.

Crystalline Form K1 and Form K2 of the compound of formula (III) are non-hydrates, as determined by Karl-Fischer measurements of weight % water, as listed in Table 10.

TABLE 10

KARL-FISCHER VALUES, K SALTS

| Form | % Water Meas. | % Water Theor. | Hydrate Form |
|---|---|---|---|
| K1 | 0.16% | 0% | non-hydrate |
| K2 | 1.09% | 0% | non-hydrate |

In another embodiment of the present invention is an amorphous form of the compound of formula (IV), more particularly Form Li1.

Amorphous Form Li1 of the compound of formula (IV) may be characterized by its physical appearance (foamy solid) and the absence of narrow peaks in the XRD (no XRD pattern).

Amorphous Form Li1 may be prepared by reacting the compound of formula (Ia) with lithium hydroxide in an organic solvent or with an alkyl lithium in an inert organic solvent under anhydrous conditions; and precipitating the product by evaporation of solvent.

In yet another embodiment of the present invention is an amorphous form of the compound of formula (V), more particularly Form Mg1.

Amorphous Form MG1 of the compound of formula (V) may be characterized by its physical properties (foamy solid) and by the absence of narrow peaks in the XRD (no XRD pattern).

Amorphous Form Mg1 may be prepared by reacting the compound of formula (Ia) with a magnesium lower alkoxide, in an organic solvent, and precipitating the product with an anti-solvent or by evaporating the solvent under reduced pressure.

In yet another embodiment of the present invention is a crystalline form of the compound of formula (VI), more particularly Form CH1.

Crystalline Form CH1 of the compound of formula (VI) may be characterized by its X-ray diffraction pattern, comprising the peaks:

TABLE 11

X-Ray Diffraction Peaks, Choline Salt, Form CH1

| Angle (°2θ) | d-spacing (Ångstrom) | Relative Intensity (%) |
|---|---|---|
| 3.033 | 29.1304 | 1.41 |
| 3.495 | 25.2817 | 0.87 |
| 4.600 | 19.2102 | 0.83 |
| 5.120 | 17.2604 | 2.36 |
| 6.518 | 13.5604 | 0.46 |
| 9.260 | 9.5511 | 2.02 |
| 10.241 | 8.6376 | 91.44 |
| 13.079 | 6.7694 | 5.45 |
| 14.019 | 6.3175 | 2.29 |
| 15.372 | 5.7643 | 18.62 |
| 16.098 | 5.058 | 5.18 |
| 17.061 | 5.1973 | 4.38 |
| 17.360 | 5.1084 | 5.79 |
| 18.540 | 4.7859 | 7.05 |
| 20.531 | 4.3260 | 100.00 |
| 22.904 | 3.8829 | 3.19 |
| 24.733 | 3.5997 | 1.67 |
| 25.723 | 3.4634 | 6.70 |
| 26.318 | 3.3864 | 2.02 |
| 27.919 | 3.1957 | 0.99 |
| 28.959 | 3.0833 | 1.07 |
| 31.054 | 2.8800 | 2.44 |
| 32.412 | 2.7623 | 0.95 |

Crystalline Form CH1 of the compound of formula (VI) may be further characterized by its X-ray diffraction pattern, comprising the major peaks:

TABLE 12

X-Ray Diffraction Peaks, Choline Salt, Form CH1

| Angle (°2θ) | d-spacing (Ångstrom) | Relative Intensity (%) |
|---|---|---|
| 10.241 | 8.6376 | 91.44 |
| 13.079 | 6.7694 | 5.45 |
| 15.372 | 5.7643 | 18.62 |
| 16.098 | 5.058 | 5.18 |
| 17.360 | 5.1084 | 5.79 |
| 18.540 | 4.7859 | 7.05 |
| 20.531 | 4.3260 | 100.00 |
| 25.723 | 3.4634 | 6.70 |

Crystalline Form CH1 of the compound of formula (VI) may be further characterized by its X-ray diffraction pattern, comprising the major peaks:

TABLE 13

X-Ray Diffraction Peaks, Choline Salt, Form CH1

| Angle (°2θ) | d-spacing (Ångstrom) | Relative Intensity (%) |
|---|---|---|
| 10.241 | 8.6376 | 91.44 |
| 15.372 | 5.7643 | 18.62 |
| 20.531 | 4.3260 | 100.00 |

Crystalline Form CH1 may be prepared by crystallizing the product from an organic solvent or mixture thereof, preferably an ethyl acetate/methanol mixture wherein the boiling point of the mixture is about 74–76° C. (i.e. wherein the percent methanol in the mixture in less than about 5%), by heating and cooling.

In yet another embodiment of the present invention is an amorphous form of the compound of formula (VI), more particularly Form CH2.

Amorphous Form CH2 of the compound of formula (VI) may be characterized by its physical properties (foamy solid).

Amorphous Form CH2 may be prepared by reacting the compound of formula (Ia) with choline hydroxide, in an organic solvent, and precipitating the product by evaporating the solvent under reduced pressure.

As used herein, the term "subject" shall refer to an animal, preferably a mammal, more preferably a human, who is the object of treatment, observation of experiment.

As used herein, the term "therapeutically effective amount", means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The salts of the instant invention may be administered to a subject in need thereof at any dosage level such that the amount is therapeutically effective. Optimal dosages to be administered may be readily determined by those skilled in the art, and will vary with the particular salt used, the mode of administration, the strength of the preparation, and the advancement of the disease condition. In addition, factors associated with the particular patient being treated, including patient age, weight, diet and time of administration, will result in the need to adjust dosages.

The present invention further provides a method of treating epilepsy in a subject in need thereof which comprises administering any of the salts as defined herein in a therapeutically effective amount. Preferably, for treating epilepsy, the salts are administered in a dosage range of about 10 to 650 mg/daily, more preferably in the range of about 16 to 325 mg/once or twice daily.

The salts of the instant invention may be administered by any suitable method, as would be apparent to one skilled in the art. More particularly, the salts of the compound of formula (I) may be administered by any parenteral method including, but not limited to, via oral, pulmonary, intraperitoneal (ip), intramuscular (im), intravenous (iv), subcutaneous (sc), transdermal, buccal, nasal, sublingual, ocular, rectal and vaginal routes of administration. The salts of the compound of formula (I) may also be administered directly to the nervous system via intracerebral, intraventricular, intracerebroventricular, intrathecal, intracisternal, intraspinal and/or peri-spinal routes of administration, with or without pump devices. It will be readily apparent to those skilled in the art that any dose or frequency of administration that provides the desired therapeutic effect is suitable for use in the instant invention.

To prepare the pharmaceutical compositions of the present invention, one or more of the salts described herein are intimately admixed with a pharmaceutical carrier according to conventional techniques, which carrier may take a wide variety of forms depending on the form of preparation desired for administration, e.g., oral, by suppository or parenteral. In preparing the compositions in oral dosage form, any of the usual pharmaceutical media may be employed. Thus, for liquid oral preparations, such as, for example, suspensions, elixers and solutions, suitable carriers and additives include water, glycols, oils, alcohols, flavoring agents, preservative, coloring agents and the like; for solid oral preparations such as, for example, powders, capsules and tablets, suitable carriers and additives include starches, sugars, diluents, granulating agents, lubricants, binders, disintegrating agents and the like. Because of their ease of administration, tablets and capsules represent the most advantageous oral dosage unit form, in which case solid pharmaceutical carriers are obviously employed. If desired, tablets may be sugar coated or enteric coated by standard techniques. Suppositories may be prepared, in which cocoa butter could be used as a carrier. For parenterals, the carrier will usually comprise sterile water, though other ingredients, for example, for purposes such as aiding solubility or for preservation, may be included. Injectable suspensions may also be prepared in which case, appropriate liquid carriers, suspending agents and the like may be employed.

The pharmaceutical compositions herein will contain, per dosage unit, e.g., tablet, capsule, powder, injection, teaspoonful, suppository and the like, from about 10 to about 500 mg of active ingredient.

The following examples describe the invention in greater detail and are intended to illustrate the invention, but not to limit it.

EXAMPLE 1

Potassium Salt—Form K2

Topiramate (853.6 mg) was dissolved in THF (2.5 mL). The solution was chilled in an ice bath. To the solution was then added 1M potassium butoxide in THF (2.5 mL) dropwise. The solution was stirred for 30 min. A precipitate was formed. The precipitate was filtered and placed in a vacuum oven at 34° C., to yield the potassium salt as Form K2, as a solid.

EXAMPLE 2

Potassium Salt—Form K2

Topiramate (1.0007 g, 2.95 mmol) was dissolved in diethyl ether (20 mL). The solution was chilled in an ice water bath under $N_2$. 1M potassium tert-butoxide in THF (2.95 mL, 2.95 mmol) was the added dropwise to the solution. The solution was stirred for 30 min and a precipitate was formed. The precipitate was filtered under N2, washed with additional diethyl ether and dried in a vacuum oven at ambient temperature to yield the potassium salt product as Form K2, as a white solid.

EXAMPLE 3

Potassium Salt—Form K3

Topiramate (0.7512 g) was dissolved in toluene (15 mL). Potassium hydroxide (0.1440 g) was added and the solution was stirred at 360 rpm. A Dean Stark trap was attached and the hot plate temperature increased until the toluene was a rapid reflux (at about 185° C.). The solution was maintained at reflux for 24 hours. The solution was allowed to cool slowly, then filtered. The remaining solvent was removed by roto-evaporation in a water bath set at 30° C. Solids remaining in the flask were dissolved in ethyl acetate (2 mL). To the solution was then added hexanes (15 mL), resulting in the formation of a precipitate. The precipitate was collected by vacuum filtration and washed with diethyl ether (30 mL), to yield the potassium salt as Form K3, as a solid. The solid was stored over $P_2O_5$.

EXAMPLE 4

Sodium Salt—Form Na1

Sodium hydride (71.1 mg) (60% dispersion in mineral oil) was rinsed 3 times with pentane and dried under $N_2$ for 30 min. A solution of topiramate (500 mg) dissolved in THF (3 mL) was added dropwise. An additional solution of topiramate (103 mg) in THF (2 mL) was then added. The solution was stirred in an ice water bath under $N_2$ overnight. To the solution was added hexane (4 mL) and the solution was again stirred overnight, resulting in the formation of a cloudy precipitate. The solution was placed in a refrigerator and then into a freezer overnight. The solution was removed from the freezer and then stirred at ambient temperature for about 3 hours. The resulting precipitate was collected by vacuum filtration and air dried to yield the sodium salt as Form Na1, as a solid.

EXAMPLE 5

Sodium Salt—Form Na3

Sodium hydride (0.1076 g) (60% dispersion in mineral oil) was rinsed with hexanes (30 mL) under $N_2$. The upper layer of the solution was removed with a dry pipette. The remaining hexanes were evaporated by fast evaporation under $N_2$ for about 1 hour. THF (2 mL) was then added to the sodium hydride slurry and the resulting slurry was cooled in an ice water bath. A solution of topiramate (853.8 mg) in THF (2.5 mL) was added dropwise to the cold sodium hydride slurry. Hexanes (25 mL) were then added to the mixture, resulting in the formation of a precipitate. The precipitate was vacuum filtered, washed with additional hexanes and then placed in a vacuum oven at 34° C. for about 1 hr.

The resulting solid was mixed with diethyl ether (40 mL) and sonicated. The solution was vacuum filtered and the precipitate dried in a vacuum oven at 34° C., to yield the sodium salt as Form Na3, as a solid.

EXAMPLE 6

Sodium Salt—Form Na4

Sodium hydride (507 mg) was rinsed 4 times with pentane (10 mL) and then allowed to dry under a $N_2$ stream. A solution of topiramate (3.5 g) in THF (10 mL) was then added to the sodium hydride and stirred at room temperature. The solution was cooled in a dry ice/isopropyl alcohol bath and then allowed to warm to room temperature. The solution was filtered through an 0.2 m nylon filter. The solution was then allowed to stand under $N_2$ stream overnight, to slowly evaporate the solvent. To the residue were added hexanes (15 mL). The resulting mixture was sonicated and the vessel sides scratched to induce precipitation of product. THF (1.5 mL) was added and the slurry stirred at ambient temperature, and let stand under $N_2$ for 2 days. The resulting precipitate was collected by vacuum filtration, rinsed 3 times with hexanes (5 mL) and placed for 6 hours in a vacuum oven at ambient temperature, to yield the sodium salt as Form Na4, as a solid. The solid was lightly ground with agate mortal and pestle prior to testing.

EXAMPLE 7

Preparation of Sodium Salt Form Na4

Topiramate (3.4 g, 10 mmol) was dissolved in THF (40 mL) at room temperature, then treated with 50% aq NaOH (0.8 g, 10 mmol). At the end of addition, a clear solution was formed. The THF was evaporated under reduced pressure and the oily residue placed under vacuum to remove any remaining solvent or water. The product formed as a white foam, an amorphous solid. XRD-analysis confirmed that the product was amorphous.

EXAMPLE 8

Preparation of Sodium Salt Form Na1

Topiramate (3.39 g, 10 mmol) in THF (50 mL) was treated with sodium ethoxide (21 wt %, 3.24 g, 10 mmol) and the mixture was stirred at room temp. The ethanol was evaporated, the residue dissolved in t-butyl methyl ether (100 mL) and treated with $H_2O$ (~0.49), resulting in the formation of a crystalline solid. The solid was collected by filtration and air-dried (3.9 g in two crops). The solid was suspended in ethyl acetate (30 mL) and heated, just enough to dissolve the solid without loosing any water. The solution was filtered quickly through a small cotton plug and allowed to stand at room temperature. The product crystallized out over about 20 min. The solid was collected by filtration, washed with a small amount of ethyl acetate and air-dried.

Water (wt % by KF): 14.2%.

EXAMPLE 9

Preparation of Sodium Salt Form Na1

Sodium hydride (95%, 0.51 g, 20 mmol) was suspended in THF (100 mL) at room temperature. Topiramate (6.78 g, 20 mmol) was added portion-wise to the suspension. At the end of addition, a nearly clear solution was formed. The solution was filtered quickly through a small cotton plug and the THF was evaporated under reduced pressure. The residue was dissolved in ethyl acetate (50 mL) and water (1 g). The solution was allowed to stand at room temperature where the product started to crystallize out, then cooled in an ice-bath. The solid was collected by filtration, washed with a small amount of ethyl acetate and air-dried.

Water (wt % by KF): 13.5%.

EXAMPLE 10

Preparation of Sodium Salt Form Na1 and Na2

Topiramate (13.56 g, 40 mmol) was dissolved in THF (120 mL) at room temperature then treated with 50% aq NaOH (3.2 g, 40 mmol). At the end of addition, a clear solution was formed. The THF was evaporated under reduced pressure and the residue was dissolved in ethyl acetate (150 mL). Water (about 2 g) was added to the solution with stirring. The product started to crystallize out soon after. The mixture was allowed to stand at room temperature for 15 min, then cooled in an ice-bath to about 5OC. The product, as Form Na1, was collected by filtration, washed with ethyl acetate and air-dried.

Water (wt % by KF): 13.58%

Recrystallization to Prepare Form Na2:

A sample of the product (3 g, 7.2 mmol) was mixed with ethyl acetate (50 mL) and heated on a steam bath until the solid dissolved. The hazy solution was hot-filtered and then allowed to stand at room temperature. The product crystallized out as a white solid; the mixture was further cooled in an ice bath. The solid was collected by filtration and rinsed with cold ethyl acetate (10 mL) then air-dried to yield the product as Form Na2.

Water 1.64 wt % by KF analysis

EXAMPLE 11

Preparation of Potassium Salt Form K1

Potassium hydroxide (85%, 0.66 g, 10 mmol) was stirred in ethanol (50 mL) at room temperature together with topiramate (3.39 g, 10 mmol). All solids dissolved in a few minutes. The solvent was evaporated under reduced pressure. The residue was dissolved in ethyl acetate (50 mL) and water (0.4 g) and allowed to stand. The solution was then cooled in an ice-bath, a white solid crystallized out. The solid was collected by filtration, washed with a small amount of ethyl acetate and air-dried.

Water (wt % by KF): 1.7%.

EXAMPLE 12

Preparation of Potassium Salt Form K1

Potassium hydroxide (85%, 0.1.32 g, 20 mmol) was dissolved in $H_2O$ (2 mL) at room temperature. Topiramate (6.78 g, 20 mmol) in ethyl acetate (75 mL) was added to the KOH and the mixture stirred at room temperature to yield a clear solution. The solvent was evaporated under reduced pressure, the residue was re-dissolved in ethyl acetate (150 mL) and allowed to stand. The solution was then cooled in an ice-bath, a white solid crystallized out. The solid was collected by filtration, washed with ethyl acetate and air-dried.

Water (wt % by KF): 0.24%.

Recrystallization:

A sample of the product (2 g, 5.3 mmol) was suspended in ethyl acetate (50 mL) and methanol (5 mL) and the mixture heated on a steam bath until the solid dissolved. Heating was continued to evaporate some of the methanol and the resulting solution was allowed to stand at room temperature. The product crystallized out as a white solid, which was collected by filtration and air-dried.

Water (wt %, by KF): 0.23%.

EXAMPLE 13

Preparation of Potassium Salt Form K1

Potassium tert-butoxide (1M in THF, 30 mmol) was added to a solution of topiramate (10.2 g, 30 mmol) in THF (75 mL) and the mixture stirred at room temperature to yield a clear solution. The solvent was evaporated under reduced pressure and the residue dissolved in ethyl acetate (150 mL) and methanol (20 mL). The solution was heated to evaporate some of the methanol (the boiling point was observed to rise from 64 to 70° C.). The solution was allowed to stand, a part of the product crystallized out. The solid was collected by filtration, washed with ethyl acetate and air-dried.

Water (wt % by KF): 0.24%

The filtrate was concentrated and allowed to stand at room temperature to yield a second crop.

EXAMPLE 14

Preparation of Potassium Salt Form K1 and K2

Potassium hydroxide (85%, 7.26 g, 110 mmol) was added at room temperature to a solution of topiramate (39 g, 115 mmol) in THF (250 mL) and methanol (50 mL). The reaction mixture was stirred at room temperature for 30 min, until all of the KOH had dissolved to yield a clear solution. The solvent was evaporated under reduced pressure and the oily residue (51.2 g) was mixed with ethyl acetate (300 mL) and methanol (15 mL) and then heated on a steam bath. The residue became a white solid, then completely dissolved to yield a clear solution. The solution was allowed to cool to room temperature, seeded with a few crystals of K-salt and left to stand at room temperature overnight. The solid was collected by filtration, washed with ethyl acetate and air-dried, to yield Form K1, as a solid.

Karl-Fischer % wt water: 0.16%

The filtrate was heated to remove most of the methanol (bp rose from 64° C. to 75° C. and the total volume was reduced to 300 mL). The solution was allowed to stand at room temperature for about 1 h, a hard white solid precipitated and was broken down before filtration. The solid was rinsed with ethyl acetate and air-dried, to yield K2 as a solid. The solid initially behaved as a hygroscopic material (became sticky) before it was air-dried; after drying there were no hygroscopic properties.

Karl-Fischer % wt water: 1.09%

EXAMPLE 15

Preparation of Potassium Salt Form K3

Potassium hydroxide (85%, 13.2 g, 200 mmol) was dissolved in water (25 mL) and added at room temperature to a solution of topiramate (68.6 g, 202 mmol) in THF (500 mL), then stirred at room temperature for 10 min. The solvent was evaporated under reduced pressure to yield a foamy solid (80.9 g). XRD analysis confirmed the solid was amorphous.

EXAMPLE 16

Preparation of Lithium Salt Form Li1 n-Butyl lithium (10 mL of 2M solution in cyclohexane, 20 mmol) was added slowly to a solution of topiramate (7.0 g, 20.6 mmol) in THF (50 mL) at about 25–35° C. The solvent was evaporated under reduced pressure to yield a foamy, light yellow, amorphous solid. XRD analysis confirmed the solid was amorphous.

EXAMPLE 17

Preparation of Magnesium Salt Form Mg1

Magnesium turnings (0.24 g 10 matm) in methanol (100 mL) were heated on a steam bath until the Mg dissolved. Topiramate (6.78 g, 20 mmol) was added to the Mg-methoxide solution and heated on a steam bath for about 5 min, then cooled to room temperature. Any contact with water was avoided. The solvent was evaporated under reduced pressure and the residue further dried under vacuum at room temperature to a constant weight, to yield the product as a white foamy amorphous solid. XRD analysis confirmed the solid was amorphous.

EXAMPLE 18

Preparation of Sodium Salt Form Na1

Topiramate (50 g, 0.147 mol) was dissolved in isopropyl acetate (600 mL) and treated with 30% NaOCH$_3$ in methanol (28.5 mL). The light yellow solution was heated at reflux to distill some of the solvent (an azeotrope of methanol/isopropyl acetate, 70.2/29.8, bp. 64° C.) till the temperature in the flask was observed to reach 85° C. The reaction mixture was then cooled to about 20–25° C. The reaction mixture was filtered through Celite (to remove any insoluble residue) and rinsed with isopropyl acetate (60 mL). The solution was then heated to 50° C. To the solution was added water (7.9 ml) over 1 min. The product was allowed to crystallize at about 20–25° C. overnight. The solid was collected by filtration, washed with isopropyl acetate (50 ml) and dried in a vacuum oven containing a bowl of water at 30° C. for 24 h.

Water (wt % by KF): 13%.

EXAMPLE 19

Preparation of Sodium Salt Form Na1

Topiramate (50 g, 0.147 mol) was dissolved in isopropyl acetate (367 ml) (2.5 L/mol). Sodium methoxide 30% in methanol (27.2 ml, 1 eq.) was added at room temperature. The mixture was stirred over 10 min and then filtered at about 22–25° C. The filtrate was then heated to 35° C. Water (8 ml, 3 eq.) was then added and the crystallization began after seeding. The mixture was cooled down to about 22–25° C. over 30 min, then further cooled down with ice-water to about 0–5° C. The precipitate was filtered off, washed with isopropyl acetate (50 ml) (0.35 L/mol) and dried at 35° C. under vacuum during 18 h.

EXAMPLE 20

Recrystallization of Potassium Salt Form K1

Solid potassium salt of topiramate (66 g; a mixture of two polymorphic forms K2 and K3) was suspended in ethanol (250 mL) and the mixture was heated to boiling until all of the solid dissolved. The hot solution was filtered through Celite and the mixture was diluted to a final volume of 360 mL with additional ethanol. The clear solution was seeded, while hot, with a few crystals of Form K1 solid and allowed to stand at room temperature without external cooling. As the solution started to cool, the solid product crystallized out slowly. The crystallization flask was kept in a refrigerator overnight and the cold mixture was filtered to isolate the solid product. The crystalline solid was rinsed with cold ethanol, then with diethyl ether and then air-dried.

The filtrate was concentrated to about 150 mL and allowed to stand at room temperature for 2 days. The resulting solid was collected by filtration, rinsed with cold ethanol and then air-dried. XRD-pattern showed Form K1.

EXAMPLE 21

Preparation of Potassium Salt Form K1

Topiramate (163.8 g, 483 mmol) was suspended in ethanol (500 mL). To the mixture was then added potassium ethoxide in ethanol (24%, 168 g, 479 mmol). Nearly all the topiramate dissolved by the end of addition (total volume ~750 mL). The initial crystallization resulted in a paste-like solid. The mixture was heated gently on a steam bath until it became fluid. Heating was then continued on a hot plate with stirring until all of the solid had dissolved. The hot solution was filtered through Celite and rinsed with hot ethanol (50 mL). The solution was again heated to boiling to form a clear solution. The solution was seeded with Form K1 crystals while hot, then allowed to stand at room temperature overnight. The flask was cooled in an ice bath for 2 h and the solid was collected by filtration. The solid was rinsed with cold ethanol (100 mL), then with diethyl ether, and then air-dried. The solid was further dried in a vacuum oven at about 40–50° C. overnight. The XRD pattern showed Form K1.

Water (wt % by KF): 0.14%

The filtrate was concentrated to about 200 mL. The solution was allowed to stand at room temperature to yield a second crop of Form K1.

EXAMPLE 22

Preparation of Choline Salt Form CH1

Topiramate (3.39 g, 10 mmol) was dissolved in ethyl acetate (100 mL) and the clear solution was treated with choline hydroxide (45% solution in methanol; 2.7 g, 10 mmol). The resulting clear solution was evaporated to dryness and the residue was kept under vacuum for 2 days. The foamy solid was dissolved in ethyl acetate (about 80 mL) which contained approximately 3 to 5 mL of methanol and the solution allowed to stand at room temperature overnight. A white crystalline solid formed, which was collected by filtration, and air-dried.

mp: 121–123° C.

A second crop (1.3 g, 29%) was obtained from the mother liquor.

Elemental analysis:

Calc'd for $C_{17}H_{34}N_2O_9S$: 46.14; H, 7.74; N, 6.33; S, 7.25 Found: C, 46.09; H, 7.72; N, 6.28; S, 7.41.

EXAMPLE 23

Preparation of Choline Salt Form CH1

Topiramate (10.36 g, 30.5 mmol) was dissolved in ethyl acetate (150 mL) and the clear solution was treated with choline hydroxide (45% solution in methanol; 8.2 g, 30.5 mmol). The solution was heated to evaporate some of the solvent while maintaining the volume constant by portionwise addition of ethyl acetate until the boiling temperature reached 75° C. The resulting clear solution was allowed to stand at room temperature overnight. The precipitated crystalline solid was collected by filtration, washed with ethyl acetate and air-dried.

mp 115–118° C. Elemental analysis: Calc'd for $C_{17}H_{34}N_2O_9S \cdot 0.17H_2O$: C, 45.83; H, 7.77; N, 6.29; S, 7.20 water, 0.69%. Found: C, 45.87; H, 8.09; N, 6.25; S, 7.14 water, wt. % by KF: 0.68%

EXAMPLE 24

Maximal Electroshock (MES) Seizure Test

Anticonvulsant activity was determined using the MES test as described by Swinyard E A, Woodhead J H, White H S, Franklin M R. Experimental selection, quantification, and evaluation of anticonvulsants. In Levy R H, et al., eds. *Antiepileptic Drugs*. $3^{rd}$ ed. New York: Raven Press, 1989: 85–102.

In this procedure, a 60-Hz alternating current (mice 50 mA, rats 150 mA) was delivered for 0.2 sec through corneal electrodes by an apparatus that is capable of precisely regulating current intensity and duration. The concave side of the electrode (2 mm diameter for mice; 4.0 mm diameter for rats) was placed on each cornea. The current reliably produces, in all rodents, a single convulsive episode that includes, as a component, hind limb tonic extension. Immediately before placement of corneal electrodes, a drop of saline (an electrolyte that promotes the dispersion of the current and that reduces lethalities) was placed on each electrode. Rodents were restrained by hand during this procedure and released immediately after stimulation to permit observation of the convulsion throughout its entire course.

The test compound or corresponding vehicle was administered to overnight fasted rodents by the oral (gavage) route of administration. (Test compound or vehicle may alternatively be administered via intraperitoneal, intravenous, subcutaneous or intramuscular route of administration.) Subsequently, electrical stimulation was administered to the rodents at a time corresponding to the suspected time of peak activity of the test compound. The test was complete when the entire course of the convulsion had been observed (typically, less than 1 minute after electrical stimulation), and rodents were then immediately euthanized by carbon dioxide inhalation.

Abolition of the hind-limb tonic extensor component of the seizure was taken as the endpoint for this test. Absence of this component indicated that the test compound has the ability to prevent the spread of seizure discharge through neural tissue. The $ED_{50}$ value of the test compound was the calculated dose required to block the hind limb tonic-extensor component of the MES-induced seizure in 50% of the rodents tested.

Form K1 of the potassium salt of topiramate (the compound of formula (Ia)) was tested in rats according to the above procedure, dosing orally. Calculated $ED_{50}$ value was determined in two separate measurements as 3.1 mg/kg and 8.1 mg/kg at 2 hours post dosing.

Form K1 of the potassium salt of topiramate (the compound of formula (Ia)) was tested in mice according to the above procedure, dosing orally and IP with calculated $ED_{50}$ results as follows:

| | |
|---|---|
| Dosing orally | ED$_{50}$ @ 2 hrs = 40.6 mg/kg |
| Dosing IP | ED$_{50}$ @ 2 hrs = 26.8 mg/kg |
| Dosing IV | ED$_{50}$ @ 5 mins = 41.51 mg/kg |

Form Na1 of the sodium salt of topiramate (the compound of formula (Ia)) was tested in rats according to the above procedure, dosing orally. Calculated ED$_{50}$ value was determined in as 4.8 mg/kg at 2 hours post dosing.

Form Na1 of the sodium salt of topiramate (the compound of formula (Ia)) was tested in mice according to the above procedure, dosing IP with calculated ED$_{50}$ results as follows:

| | |
|---|---|
| Dosing IP | ED$_{50}$ @ 30 mins = 45.44 mg/kg |
| Dosing IV | ED$_{50}$ @ 5 mins = 46.18 mg/kg |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A crystalline choline salt of a compound of formula (I)

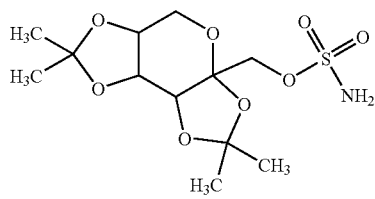

(I)

wherein a choline cation displaces one hydrogen atom of the sulfamate, and wherein the salt has the following structure:

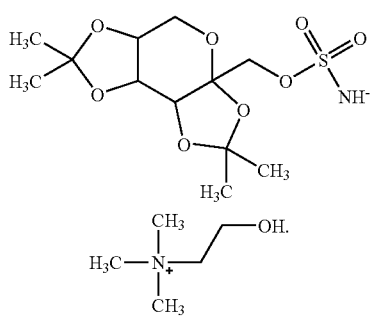

2. The salt as in claim 1, of the formula (VI)

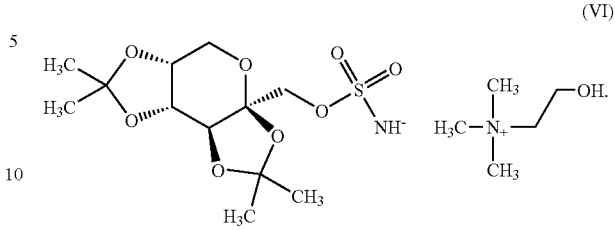

(VI)

3. A salt as in claim 2, characterized essentially by the following X-ray diffraction pattern:

| Angle (°2θ) | d-spacing (Ångstrom) | Relative Intensity (%) |
|---|---|---|
| 3.033 | 29.1304 | 1.41 |
| 3.495 | 25.2817 | 0.87 |
| 4.600 | 19.2102 | 0.83 |
| 5.120 | 17.2604 | 2.36 |
| 6.518 | 13.5604 | 0.46 |
| 9.260 | 9.5511 | 2.02 |
| 10.241 | 8.6376 | 91.44 |
| 13.079 | 6.7694 | 5.45 |
| 14.019 | 6.3175 | 2.29 |
| 15.372 | 5.7643 | 18.62 |
| 16.098 | 5.058 | 5.18 |
| 17.061 | 5.1973 | 4.38 |
| 17.360 | 5.1084 | 5.79 |
| 18.540 | 4.7859 | 7.05 |
| 20.531 | 4.3260 | 100.00 |
| 22.904 | 3.8829 | 3.19 |
| 24.733 | 3.5997 | 1.67 |
| 25.723 | 3.4634 | 6.70 |
| 26.318 | 3.3864 | 2.02 |
| 27.919 | 3.1957 | 0.99 |
| 28.959 | 3.0833 | 1.07 |
| 31.054 | 2.8800 | 2.44 |
| 32.412 | 2.7623 | 0.95 |

4. A salt as in claim 2, characterized essentially by the following X-ray diffraction pattern:

| Angle (°2θ) | d-spacing (Ångstrom) | Relative Intensity (%) |
|---|---|---|
| 10.241 | 8.6376 | 91.44 |
| 13.079 | 6.7694 | 5.45 |
| 15.372 | 5.7643 | 18.62 |
| 16.098 | 5.058 | 5.18 |
| 17.360 | 5.1084 | 5.79 |
| 18.540 | 4.7859 | 7.05 |
| 20.531 | 4.3260 | 100.00 |
| 25.723 | 3.4634 | 6.70 |

5. The salt as in claim 2, characterized essentially by the following X-ray diffraction pattern:

| Angle (°2θ) | d-spacing (Ångstrom) | Relative Intensity (%) |
|---|---|---|
| 10.241 | 8.6376 | 91.44 |
| 15.372 | 5.7643 | 18.62 |
| 20.531 | 4.3260 | 100.00 |

6. A pharmaceutical composition comprising a salt of claim 1 and a pharmaceutically acceptable carrier.

7. A process for making a pharmaceutical composition comprising combining a salt of claim 1 with a pharmaceutically acceptable carrier.

8. A process for preparing a choline salt of a compound of formula (I) comprising reacting a compound of formula (I)

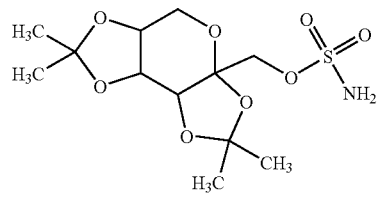

(I)

with choline hydroxide, in an organic solvent; and precipitating the product.

9. The process as in claim 8, wherein the compound of formula (I) is topiramate of the formula:

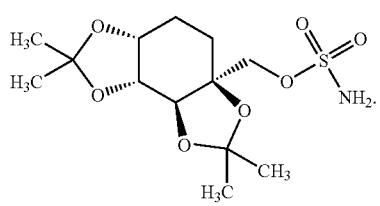

(Ia)

* * * * *